United States Patent [19]

McGary et al.

[11] Patent Number: 4,676,975
[45] Date of Patent: Jun. 30, 1987

[54] THERMOPLASTIC POLYURETHANE ANTICOAGULANT ALLOY COATING

[75] Inventors: Charles W. McGary, Centerville; Donald D. Solomon, Spring Valley, both of Ohio

[73] Assignee: Becton, Dickinson and Company, Franklin Lakes, N.J.

[21] Appl. No.: 679,160

[22] Filed: Dec. 7, 1984

[51] Int. Cl.$^4$ .................. C08L 5/10; A61K 31/75
[52] U.S. Cl. ..................... 424/423; 424/423; 514/24; 514/56; 514/822; 514/929; 523/112; 128/DIG. 22; 604/304
[58] Field of Search ............ 424/25, 31, 32, 35; 514/24, 56, 822, 929; 128/DIG. 22; 604/304; 523/112

[56] References Cited

U.S. PATENT DOCUMENTS

| | | | |
|---|---|---|---|
| 3,457,098 | 7/1969 | Leininger et al. | 117/62.1 |
| 3,617,344 | 11/1971 | Leininger et al. | 117/47 |
| 3,844,989 | 10/1974 | Harumuya . | |
| 3,846,353 | 11/1974 | Grotta | 424/183 |
| 3,853,804 | 12/1974 | Yen . | |
| 4,118,485 | 10/1978 | Eriksson et al. | 424/183 |
| 4,302,368 | 11/1981 | Dudley et al. | 523/112 |
| 4,349,467 | 9/1982 | Williams et al. | 523/112 |

FOREIGN PATENT DOCUMENTS

2364939  9/1975  France ................ 523/112

OTHER PUBLICATIONS

Larm et al, "New N.m. Thrombogenic Surface Prepared by Selective Covalent Binding of Heparin . . .", Biomat., Med Dev., Art., Org. 11 (283), pp. 161–173 (1983).

Grode, G. A. et al., J. Biomed. Mat. Res. Symp. No. 3, pp. 77–84, (1972).

Primary Examiner—John Kight
Assistant Examiner—Nathan M. Nutter
Attorney, Agent, or Firm—Robert P. Grindle

[57] ABSTRACT

An antithrombogenic thermoplastic polyurethane product and process for preparing the same which comprises a substrate and at least one layer of a polyurethane alloy complex comprising a thermoplastic polyurethane and completely dispersed therein a preformed complex of an antithrombogenic material ionically bonded with a quaternary ammonium compound.

13 Claims, 2 Drawing Figures

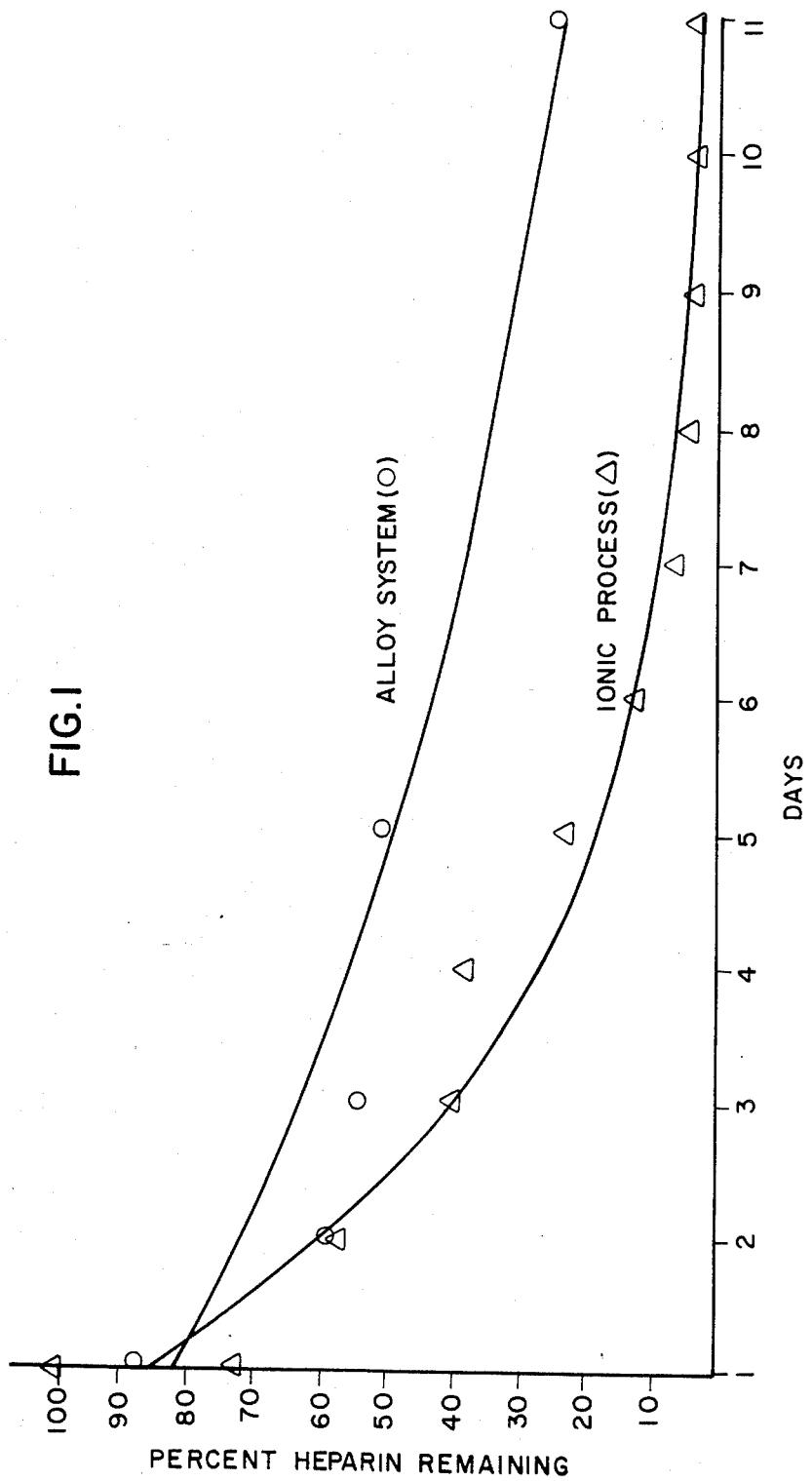

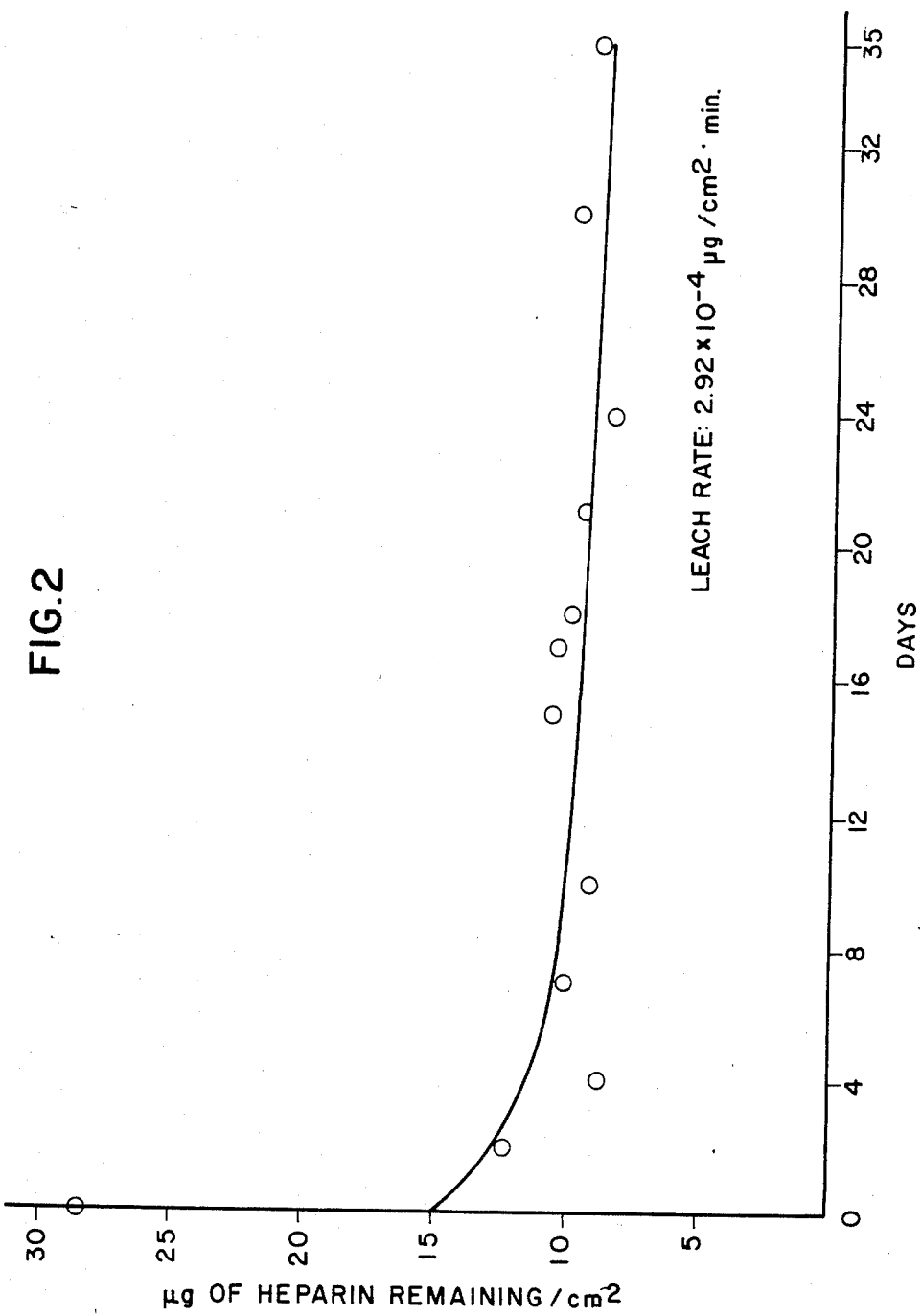

THERMOPLASTIC POLYURETHANE ANTICOAGULANT ALLOY COATING

The present invention relates to a novel antithrombogenic thermoplastic polyurethane product and process for making the same. More particularly the invention relates to a polyurethane product having an antithrombogenic alloy complex material bound thereto so that the material is permanently affixed to the polyurethane substrate and remains leachable over prolonged periods when the products are in use.

Extensive investigations have been undertaken over many years to find materials that will be biologically and chemically stable towards body fluids. This area of research has become increasingly important with the development of various objects and articles which can be in contact with blood, such as artificial organs, vascular grafts, probes, cannulas, catheters, hyperalimentation catheters and other long indwelling vascular catheters, and the like.

Artificial materials are being increasingly used as blood contact devices and may be subject to potential generation of thrombus. When blood contacts foreign materials a complex series of events occur. These involve protein deposition, cellular adhesion and aggregation, and activation of blood coagulation schemes. Considerable research effort has been focused on this blood-material-interaction in the last twenty years. The overall objective of these investigations has been to minimize the potential for thrombus formation on the foreign materials, such as the device when introduced into the body upon contact with blood.

Various methods have been devised for producing such a material, most of which involve chemically bonding a quaternary ammonium salt to the polymer and then heparinizing the same. Usually, this is done by incorporating an amine in the polymer, quaternizing the amine, and then heparinizing the quaternized material.

In one method taught by R. I. Leininger and G. A. Grode, U.S. Pat. No. 3,457,098, a quaternary amine is incorporated into an epoxy resin. Subsequent exposure to sodium heparinate then results in ionically bound heparin. The polymer systems are essentially epoxy resins which are rigid polymers which are not suitable for forming medical devices such as catheters or other devices requiring extrusion. These polymers also are not appropriate where flexibility in the device is required.

R. I. Leininger and R. D. Falb, disclose in U.S. Pat. No. 3,617,344 another process for binding heparin. This system differs from the previous system, in that, low molecular weight chloromethyl groups are adsorbed to the surface of a polymer substrate. Subsequent amination by a tertiary amine and quarternization resulted in a positively charged surface for binding with heparin. The concept, in general, embodies the use of low molecular weight quaternized groups to ionically bind heparin.

U.S. Pat. No. 3,846,353 to Grotta involves use of long chain alkyl quaternary amines on the surface of a polymer wherein the positively charged surface is exposed to a solution of sodium heparinate. This resulted in ionically bound heparin. Example VII of this patent discusses the preparation of a complex of tridodecylmethyl ammonium chloride (TDMAC) and sodium heparinate. The latter is commonly known as the one-step TDMAC-Heparin process. An article by G. A. Grove (J. Biomed. Mat. Res. Symp. No. 3, PP. 7784, 1972) describes this method in more detail. The resultant coating from the Grotta method is a waxy leachable anticoagulant surface. The primary deficiency of the Grotta method is that the coating has relatively short-lived anticoagulant efficacy.

S-P.S. Yen and A. Rembaum prepared a neutral polyurethane elastomer which is subsequently quaternized and ionically bonded to heparin, U.S. Pat. No. 3,853,804. The main disadvantage of this system is that it is a chemical complex and toxic solvents are used to achieve solubilitY when coating (see Example 8). The coating technique, however, is difficult to perform due to the solvent (DMF) requirement. The patent of N. Harumiya et al. U.S. Pat. No. 3,844,989 describes a polymer composition of water-insoluble cationic copolymers having hydrophilic components, quaternary amine groups, and hydrophobic moieties. Heparin is bonded ionically to the quaternary ammonium groups via absorption after the polymer components are contacted with a heparin solution. This method consists of complex synthesis procedures and is not readily applicable to coating other polymeric or non-polymeric materials.

It would be desirable to provide a material which has excellent biological and chemical stability towards body fluids, namely blood and which retains its antithrombogenic agent for a long term while being slowly leachable when in contact with blood. It would also be desirable to provide materials which, while being biocompatible, are also biofunctional, that is materials which have biological activity in a variety of functions.

The present invention accomplishes all of these needs by use of an antithrombogenic thermoplastic polyurethane alloy system. More particularly the invention involves an antithrombogenic polyurethane product having an antithrombogenic thermoplastic polyurethane product, which comprises: a polyurethane substrate and at least one layer of a polyurethane alloy complex comprising a second thermoplastic polyurethane and completely dispersed therein a preformed complex of an antithrombogenic material ionically bonded with a quaternary ammonium compound.

In another embodiment, the present invention involves a process for imparting antithrombogenic activity to polyurethane materials. This process involves preparing a slow release antithrombogenic polyurethane product by contacting a preformed polyurethane substrate with an organic solvent having dissolved therein a thermoplastic polyurethane and a formed complex of the antithrombogenic material and a quaternary ammonium compound; conducting the contacting for a sufficient time to form a thin film of the alloy complex upon the polyurethane substrate and removing the solvent to form the resulting product.

The term antithrombogenic agent or material as used herein refers to any material which inhibits thrombus formation on its surface, such as by reducing platelet aggregation, dissolving fibrin, enhancing passivating protein deposition, or inhibiting one or more steps within the coagulation cascade and which form an ionic complex with quaternary ammonium salts. Illustrative antithrombogenic materials may be selected from the group consisting of heparin, prostaglandins, sulfated polysaccharide, and mixtures thereof. Heparin is preferred. In addition to the foregoing antithrombogenic agents, optional supplemental amounts of antithrombogenic agents may also be used that are not reactive within the scope of the invention to further enhance the effects of the alloy complexed materials. Exemplary materials include urokinase, streptokinase, albumin and so forth.

The alloy system of this invention is an improvement over other ionic/leachable antithrombogenic systems. By combining the quaternary ammonium heparin complex with the thermoplastic polyurethane coating the permanency of the heparin coating is significantly enhanced. In vitro permanency testing under severe ionic conditions and in vitro coagulation testing both demonstrate a substantial increase in permanency of the alloy system over the one-step ionic process with no reduction in antithrombogenic activity. The composition and process of this invention may be used to effect a durable antithrombogenic coating on polymer surfaces. The antithrombogenic coated polymers impart non-thromobogenic character and have the potential to reduce thromboembolic complications commonly associated with long term in-dwelling catheters.

The polyurethane polymers used in the invention as the support structure may be selected from a wide range of thermoplastic polyurethane polymers. The particular formations do not constitute a critical aspect of this invention other than to serve as a support substrate for the antithrombogenic alloy complex. The polyurethanes are preferably preformed into the desired shape or structure for the particular application prior to treatment according to the invention. Of significant importance is the ability of the polyurethane support to adhere with the antithrombogenic alloy complex without becoming deformed when the complex is applied to the substrate. It has been found that polyurethane polymers may be useable as supports which have average molecular weights different from the polyurethanes used to form the alloy complex and which permit the polyurethane support to not dissolve in the organic solvent for the complex. This distinction is critical to enable coating of preformed supports without deformation while permitting a layer of alloy complex to be chemically coupled to the support structure. In this manner, an integral unit is formed which will not separate upon use.

The antithrombogenic alloy complex is formed by dissolving in an organic solvent the antithrombogenic agent and a suitable polyurethane polymer. When the preferred antithrombogenic agent is heparin which is soluble for all practical purposes only in water, only a poor dispersion results when heparin is mixed in organic solvents. Accordingly, it is necessary to modify the heparin to render it soluble in the organic solvent. This is done by reacting the heparin, in an aqueous solution, with a primary alkylammonium salt in an organic solvent to form a heparinalkylammonium complex compound having a low water solubility. It is desired to let this reaction proceed so far so that substantially all the anionic groups in the heparin molecule have reacted with the alkylammonium ions. The best way of having the reaction proceed so far as to produce complete blocking is to have the alkylammonium salt be present in a quantity at least corresponding to the number of heparin anionic groups which are present in the solution from which the complex can be separated into the organic phase.

A particularly preferred family of quaternary ammonium compounds useable in the invention are long chain alkyl quaternary ammonium salts of heparin. The salt may have 2 to 4 long chain alkyl groups attached to the nitrogen atom, the alkyl groups having from about 10 to about 30 carbon atoms. The alkyl groups can be like or unlike. The remaining groups may be hydrogen, lower alkyl, aryl and aryl alkyl groups. These compounds are generally obtained by heating together a tertiary amine and an alkylating agent to thereby produce the quarternary ammonium salt by standard techniques well known to the ordinary skilled artisan. Preferred quaternary ammonium compounds are selected from the group consisting of tridodecylmethyl ammonium salts, and tetradodecyl ammonium salts and mixtures thereof.

The alloy coating system may be prepared from any suitable organic solvent that is capable of dissolving both the antithrombogenic agent and the second polyurethane polymer without chemically modifying either material. Preferred solvents have high vapor pressure which aids in reducing solvent evaporation/drying time. Exemplary, non-limiting compounds include hexane and methylene chloride.

The alloy system is prepared such that the final weight ratio of thermoplastic polyurethane to antithrombogenic agent is 10:1 to 1:5, preferably from 4:1 to 1:2 and most preferably 2:1 to 1:1. At ratios above 10:1 there is insufficient antithrombogenic agent present to provide antithrombogenic efficacy. At ratios below 1:5 insufficient polyurethane is present to provide a suitable film coating.

The polyurethane polymers used to form the support as well as the alloy complex may be selected from a wide range of materials which contain conventional polyisocyanates, low molecular weight glycols and high molecular weight glycols.

The polyisocyanates useful in the invention in introducing the urethane linkage into the polymer chain may be selected from a wide range of aliphatic, cycloaliphatic and aromatic polyisocyanates. Useable diisocyanates may contain noninterfering groups, e.g., aliphatic hydrocarbon radicals such as lower alkyl or other groups, having substantially nonreactive hydrogens as determined by the Zerewitinoff test, J. Am. Chem. Soc. 49,3181 (1927). The diisocyanate often has at least 6 carbon atoms and usually does not have more than about 40 carbon atoms. Diisocyanates of about 8 to 20 atoms in the hydrocarbon group are preferred. Suitable diisocyanates include 2,4-toluene diisocyanate; 2,6toluene diisocyanate; 1,4-cyclohexane diisocyanate; dicyclohexylmethane 4,4'-diisocyanate; xylene diisocyanate; 1-isocyanate-3-isocyanatomethyl-3,5,5-trimethylcyclohexane; hexamethylene diisocyanate; methylcyclohexyl diisocyanate; 2,4,4-trimethylhexyl-methylene diisocyanate, isocyanates such as m-phenylene diisocyanate; mixtures of 2,4- and 2,6 hexamethylene-1,5-diisocyanate; hexahydrotolylene diisocyanate (and isomers), naphtylene-1,5-diisocyanate 1-methoxyphenyl 2,4-dissocyanate, diphenylmethane 4,4'-diisocyanate, 4,4'-biphenylene diisocyanate, 3,3'-dimethoxy-4.4biphenyl diisocyanate, 3,3' dimethyl - 4,4'-biphenyl diisocyanate, and 3,3'dimethyl-diphenylmethane - 4,4'diisocyanate and mixtures thereof. The aliphatic and alicyclic diisocyanates employed in the process of this invention and the products made therefrom generally exhibit good resistance to the degradative effects of ultraviolet light.

The polyisocyanate component used to form the prepolymers may contain a portion of polyisocyanates having more than two isocyanate (NCO) groups per molecule providing the urethane polymer compositions are not unduly deleteriously affected. The preferred polyisocyanate is selected from the group consisting of 4,4'-diphenylmethane diisocyanate, toluene diisocyanate, isophorone diisocyanate and methylene bis (4-cyclohexyl) diisocyanate.

The low molecular weight glycols may also be used to prepare the prepolymer which materials may have from 2 to 10 carbon atoms. Exemplary of these glycols are ethylene glycol, diethylene glycol, triethylene glycols, 1,4-butanediol, neopentyl glycol, 1,6-hexanediol, 1,2- and 1,3-propylene glycol, 2,3-butylene glycol, cyclohexane dimethanol (1,4-bis hydroxymethyl cyclohexane), dipropylene glycol, and dibutylene glycol.

The high molecular weight glycols useful in the present invention may be a polyether diol or polyester diol and range in number average molecular weight from about 400 to about 3,000 and preferably about 500 to about 2,000. Exemplary of the polyols which may be employed to prepare polyester polyols are 1,6-hexanediol, neopentyl trimethylol propane, ethylene glycol, diethylene glycol, triethylene glycol, 1,4-butanediol, 1,4-cyclohexane, 1,2-propanediol, 1,3-propanediol, 1,3-butylene glycol, 1,4-cyclohexane dimethanol, 1,6-hexanediol, and the like, and mixtures thereof. Illustrative polyesters may contain hydroxyl groups, for example, reaction products of polyhydric alcohols reacted with divalent carboxylic acids. It is also possible to use the corresponding polycarboxylic acid anhydrides or corresponding polycarboxylic acid esters of lower alcohols or mixtures thereof, for producing the polyesters. The polycarboxylic acids may be aliphatic, cycloaliphatic, aromatic and/or heterocyclic and may optionally be substituted, for example, by halogen atoms and/or unsaturated. Examples of polycarboxylic acids of this kind include succinic acid, adipic acid, suberic acid, azelaic acid, sebacic acid, phthalic acid, phthalic acid anhydride, tetrachlorophthalic acid anhydride, endomethylene tetrahydrophthalic acid anhydride, glutaric acid anhydride, maleic acid, maleic acid anhydride, fumaric acid, dimeric and trimeric fatty acids such as oleic acid, optionally in admixture with monomeric fatty acids, terephthalic acid dimethyl ester and terephthalic acid dimethyl ester and terephthalic acid bis-glycol ester. Examples of suitable polyhydric alcohols are ethylene glycol, 1,2- and 1,3-propylene glycol, 1,4- and 2,3-butylene glycol, 1,6-hexane diol, 1,8-octane diol, neopentyl glycol, cyclonexane dimethanol (1,4-bis-hydroxy methyl cyclohexane), 2-methyl-1,3-propane diol, also diethylene glycol, triethylene glycol, tetraethylene glycol, polyethylene glycols, dipropylene glycol, polypropylene glycols, dibutylene glycol and polybutylene glycols. Polyesters of lactones, for example, epsoloncaprolactone or hydroxy carboxylic acids, for example, w-hydroxycaproic acid, may also be used.

The polyethers containing at least 2, generally 2 to 8, but preferably 2 to 3 hydroxyl groups used in accordance with the invention are also known per se and are obtained, for example, by polymerizing epoxides, such as ethylene oxide, propylene oxide, butylene oxide, tetrahydrofuran, styrene oxide or epichlorohydrin on their own, for example, in the presence of $BF_3$, or by adding these epoxides, optionally in admixture or in succession, to starter components containing reactive hydrogen atoms, such as water, alcohols, or amines, for example, ethylene glycol, 1,3- or 1,2-propylene glycol, 4,4'-dihydroxy diphenyl propane, aniline, ammonia, ethanolamine or ethylene diamine. The most preferred polyether diol are poly(tetramethylene ether) glycols.

While the preferred polyurethane compositions of the invention are thermoplastic in order to enable the urethane to be dissolved so that the alloy complex may be formed, it has been found possible to employ small amounts of crosslinking agents to the compositions when the alloy complex is being coated onto the support in order to render them thermosetting. Suitable crosslinking agents are discussed above and include the listed diisocyanate compounds.

Once prepared, the polyurethane and antithrombogenic agent are dissolved in a solvent at the appropriate concentration of about 0.1% to about 40%, and preferably 0.5 to 5% respectively, the polyurethane substrate is contacted with the alloy system to form a layer of alloy upon the polymer substrate. The time needed to perform the contacting may vary widely depending upon the substrate solvent, and alloy thickness desired. It has been found that coating thicknesses, i.e., films of 0.1 to 5 mils are obtained when the polyurethane substrate is dipped into the alloy system and depending upon the withdrawn rate. Obviously, faster withdrawals result in thicker films while slower withdrawals result in thinner films.

Once the polyurethane product is withdrawn, the solvent is removed, such as by flashing off in the presence or absence of heat.

While the present invention has been described in terms of using polyurethane polymers as the support surface, it should be recognized that other solid support materials could be used. Exemplary materials include polyamides, polyesters, polyvinyl chlorides, metal or glass.

It should be recognized that the antithrombogenic thermoplastic polyurethane products of this invention are useable in a wide variety of devices designed for contacting body fluids. Exemplary articles which can be in contact with body fluids such as blood, include artificial organs, vascular grafts, probes, cannulas, catheters, hemodialysis tubing, hyperalimentation catheters and other long indwelling vascular catheters, and the like. A particularly preferred application. The thermoplastic polyurethane products of the invention is in catheter type devices wherein the alloy complex may be coated on either or both interior and exterior surfaces of the catheter.

The invention will be further illustrated by the following non-limiting examples. All parts and percentages given throughout the specification are by weight unless otherwise indicated.

EXAMPLE 1

This example demonstrates the preparation and leach rate of structures of the invention using heparin coupled with tridodecylmethyl ammonium chloride (TDMAC) as the antithrombogenic agent compared to surface treated material.

The anticoagulant alloy was prepared by the following procedure: Heparin (4.5 g) was dissolved in 100 ml. of water and placed with TDMAC (7.0 g) dissolved in toluene/petroleum either (1:1 by volume) into a separatory funnel. The solutions were vigorously mixed for two minutes. The reaction vessel was allowed to stand overnight and then the organic phase containing the TDMAC-heparin was collected and evaporated into a beaker under nitrogen.

A thermoplastic polyurethane was formulated such that it could be dissolved in a solvent which would not destroy the integrity of the item to be coated, in this case polyurethane catheter tubing. An appropriate solvent such as methylene chloride was chosen as the "Alloy" solvent.

The alloy solution was prepared such that the final concentration was 1% TPU and 1% TDMAC-heparin (isotopically labeled). Polyurethane catheter tubing (16 gauge) was dipped into the alloy solution and withdrawn at the rate of 21 cm/sec. This resulted in a coating thickness of approximately 0.7 mil. The coated polyurethane catheter tubing was allowed to stand 30 minutes to flash off residual solvent. Catheter sections (12 cm.) were placed in 3M NaCl for up to ten days. At specified intervals sections were removed, rinsed in distilled water, and placed into scintillation vials. Ten milliliters of solvent were then added to dissolve the polymer and alloy. After dissolution, 10 ml. of scintillation solution were added and the sample placed in a Packard Tricarb scintillation counter for analysis.

Figure I shows the results. The Alloy System is compared to the one-step process surface coating where both systems started with approximately the same amount of heparin. In the comparative example the polyurethane surface was treated with TDMAC-Heparin followed by treatment with the antithrombogenic agent. The results shows a substantial increase in permanency over the comparative process. After 10 days of leaching, 24% of the heparin in the alloy coating remains whereas the comparative process contained less than 3%.

EXAMPLE 2

This example demonstrates the low sustained release of the structures of this invention using the same alloy as that of the previous example. Thermoplastic polyurethane "thimbles" were solution cast to form the test environment. These thimbles were then coated with a TDMAC-heparin complex (comparative system). The amount of heparin was found to be 33.5 $\mu g/cm^2$. An alloy of TPU and TDMAC-heparin complex was prepared. The thimbles were cast from an 18% thermoplastic polyurethane solution in THF onto glass test tubes. The thimbles were manually dipped in a 1% solution of the alloy in methylene chloride. After drying, the thimbles were stripped from the glass tubes, inverted, and cut to size, leaving the alloy coating on the inner surface of the thimbles.

The amount of heparin applied was very similar to the levels applied using the comparative system, 32.9 $\mu g/cm^2$. Each set of anticoagulant coated thimbles were placed in a separate 1.0 liter container of 3 Molar NaCl solution. The solutions were then agitated at room temperature and the samples were removed as needed for testing. The thimbles were examined at intervals from 2 to 35 days.

Figure II shows the results. After three to four days in 3 Molar saline, the release of heparin levels out to a low leach rate of $2.92 \times 10^{-4}$ $\mu g/cm^2$ min. This is approximately 100 times less than the comparative system.

EXAMPLE 3

This example demonstrates the anticoagulant efficacy of this invention over long periods of time. A 3 Molar saline solution is used to challenge the system of this invention. Since blood is 0.85% saline, a 3 Molar saline solution presents a much stronger challenge to an ionically releasing system.

Thimbles of the comparative system and thimbles coated with alloy as described in Example 2 were prepared. The difference being that no radiolabeled heparin was used in this example.

Both comparative and alloy thimbles were placed in 3 Molar saline solution. At the appointed test interval, a sample was removed from the 3M NaCl solution, it was rinsed with distilled water and dried in a desiccator before testing. Partial thromboplastin times (PTT) were determined for each thimble by the following procedure:

(a) The thimble was placed in a heating block well in a water bath at 37° C.

(b) 0.1 ml. fresh, citrated, platelet-poor plasma and 0.1 ml. partial thromboplastin reagent were pipetted into a thimble and incubated for five minutes.

(c) 0.1 ml. of 0.02M CaC12 was added and a stopwatch was started simultaneously.

(d) A nichrome loop was passed through the plasma mixture at a rate of two sweeps per second until the first strands of fibrin are detected.

PTT's were performed on glass test tubes and uncoated TPU thimbles on each test day as controls. Table I shows a comparison of the partial thromboplastin times obtained for the comparative ionic process and the Alloy System. Glass and uncoated TPU served as controls.

The study was designed to apply approximately the same amount of heparin to a polymer surface using both methods, comparative and the Alloy System. Not only is there heparin remaining in the alloy coating after 8 months, but it sill retains its anticoagulant activity. The partial thromboplastin times in Table I point out the advantage of the alloy system over the comparative Ionic Process. After sixteen days in 3M saline the ionic coating was unable to extend the PTT beyond that of the TPU controls (x=161 sec.). The alloy coating extended the PTT more than ten times that of the TPU control even after seven months in 3M saline. In the case of the PTT test, a coagulation time longer than control (uncoated TPU) indicates an anticoagulant effect.

TABLE I

TPU/TDMAC-HEPARIN ALLOY VS. IONIC ONE-STEP PROCESS DEPLETION STUDY IN 3M SALINE WITH COATED THIMBLES

| Leach Times (Days) | PTT TIMES (sec.) | | | |
|---|---|---|---|---|
| | Ionic Process | Alloy System | Glass Control | TPU Only Control |
| 0 | >1800 | >1800 | 58 | 154 |
| 3 | >1800 | >1800 | 58 | 154 |
| 7 | 1128 | >1800 | 61 | 131 |
| 10 | 228 | >1800 | 59 | 153 |
| 15 | 189 | >1800 | 62 | 180 |
| 17 | 128 | >1800 | 63 | 139 |
| 18 | 167 | >1800 | 67 | 161 |
| 21 | — | >1800 | 67 | 161 |
| 24 | — | >1800 | 65 | 201 |
| 30 | — | >1800 | 58 | 168 |
| 35 | — | >1800 | 58 | 167 |
| 210 | — | >1800 | 60 | 181 |
| 240 | — | >1800 | 59 | 179 |

EXAMPLE 4

This example demonstrates the wide latitude in the ratio of TPU to anticoagulant agent which can be employed in this invention. Thimbles of the comparative system and thimbles coated with alloy as described in Example 2 were prepared. Alloy solutions were prepared in four ratios using a low hard segment thermoplastic polyurethane dissolved in methylene chloride and TDMAC-heparin in 50:50 toluene-petroleum ether.

The results are set forth in Table II show an anticoagulant effect as measured by the partial thromboplastin time (PTT) test for all alloy ratios of TPU to TDMAC-heparin.

TABLE II

|  | Control Glass | Control Uncoated Polyurethane Thimble | ALLOY COATED THIMBLES (TPU: TDMAC-HEPARIN) | | | |
| --- | --- | --- | --- | --- | --- | --- |
|  |  |  | 4:1 | 3:1 | 2:1 | 1:2 |
| PTT Time | 67 sec. | 179 sec. | >1800 sec | >1800 sec | >1800 sec | >1800 sec |

EXAMPLE 5

This example demonstrates that the Alloy System of this invention can be crosslinked to achieve a longer sustained release of anticoagulant. Diisocyanates were added to the 1:1 alloy of TPU: TDMAC-heparin in the following ratios: 0.05%, 0.15%, and 0.50%. Diisocyanates can be chosen from any of those currently available commercially by those skilled in the art. For this example, MDI was chosen. Radiolabeled heparin was used to quantitate the percentage leached with each ratio of added diisocyanate. Thimbles were coated using similar techniques to those of Example 2. After flashing off the coating solvent the samples were placed in 3M saline. A comparison of percentage heparin remaining after 240 hours is shown in Table III.

This experiment clearly demonstrated the potential for decreasing the leach rate while still maintaining the anticoagulant effect in the alloy through the additional crosslinking agents.

TABLE III

|  | Alloy | 0.05% MDI in Alloy | 0.15% MDI in Alloy | 0.05% MDI in Alloy |
| --- | --- | --- | --- | --- |
| ug Heparin/cm$^2$ | 49.07 | 42.44 | 39.71 | 36.47 |
| % Heparin remaining @ 240 hr. in 3 M saline | 23.6% | 35.8% | 54.7% | 86.8% |
| % Increase in permanency over alloy | — | 51.7% | 131.8% | 267.8% |
| PTT | >1800 sec | >1800 sec | >1800 sec | TPU control (x = 161 sec) |

The invention being thus described, it will be obvious that the same may be varied in many ways. Such variations are not to be regarded as a departure from the spirit of scope of the invention and all such modifications are intended to be included within the scope of the claims.

We claim:

1. A thermoplastic polyurethane product possessing long-term antithrombogenic properties, comprising
    (a) a polyurethane alloy complex formed in an organic solvent solution;
    (b) said polyurethane alloy complex including
        (1) a thermoplastic polyurethane;
        (2) a material dispersed throughout said thermoplastic polyurethane;
        (3) said dispersed material being an antithrombogenic material;
        (4) said dispersed material ionically bonded to said thermoplastic polyurethane by a quaternary ammonium compound;
    (c) a solid polyurethane substrate separate from said thermoplastic polyurethane in said polyurethane alloy complex comprised of a material not soluble in said organic solvent solution for said polyurethane alloy complex; and
    (d) said polyurethane alloy complex being in the form of a surface layer on said polyurethane substrate.

2. The thermoplastic polyurethane product of claim 1, wherein
    the weight ratio of said thermoplastic polyurethane to said dispersed material is within the range of between about 10:1 and 1:5.

3. The antithrombogenic thermoplastic polyurethane product of claim 1 wherein the antithrombogenic material is selected from the group consisting of heparin, prostaglandins, sulfated polysaccharide, and mixtures thereof.

4. The antithrombogenic thermoplastic polyurethane product of claim 1 wherein the quaternary ammonium compound is a long-chain alkyl quaternary ammonium salt having from 2 to 4 alkyl groups each having from about 10 to about 30 carbon atoms.

5. The antithrombogenic, thermoplastic polyurethane product of claim 1 wherein the quaternary ammonium compound is selected from the group consisting of tridodecylmethyl ammonium salts, tetradodecyl ammonium salts and tridodecylbenzyl ammonium salts.

6. The antithrombogenic thermoplastic polyurethane product of claim 1 wherein a crosslinking agent is employed to render the polyurethane product thermosetting in nature.

7. A method for producing a thermoplastic polyurethane product possessing long-term antithrombogenic properties, comprising the steps of
    (a) selecting a thermoplastic polyurethane;
    (b) selecting an antithrombogenic material;
    (c) selecting a quaternary ammonium compound;
    (d) coupling said material from step (b) with said quaternary ammonium compound from (c);
    (e) adding said thermoplastic polyurethane from step (a) and said material from step (d) to an organic solvent solution;
    (f) dispersing said material step (d) throughout said material from step (a) to form a polyurethane alloy complex solution;
    (g) selecting a solid article comprised of a polyurethane not soluble in said organic solvent solution from step (e)
    (h) coating the surface of said solid article from step (g) with said solution from step (f); and
    (i) removing said solvent solution from the coated surface formed in step (h) to form a solid substrate of said article comprised of polyurethane having disposed on the surface thereof a layer of an alloy complex including polyurethane separate from the polyurethane in said article.

8. The method of claim 2, wherein said article selected in step (g) is a vascular catheter.

9. The method of claim 7 wherein the antithrombogenic material is selected from the group consisting of heparin, prostaglandins, sulfated polysaccharide, and mixtures thereof.

10. The method of claim 7 wherein the quaternary ammonium compound is a long chain alkyl quaternary ammonium salt having from 2 to 4 alkyl groups each having from about 10 to about 30 carbon atoms.

11. The method of claim 7 wherein the quaternary ammonium compound is selected from the group consisting of tridodecylmethyl ammonium salts, tetradodecyl ammonium salts, and tridodecylbenzyl ammonium salts.

12. The method of claim 7 wherein the contacting is performed by dipping the substrate into the organic solvent containing the prefromed complex.

13. The method of claim 7 wherein the solvent is removed from the polyurethane product by heating the product to volatize the solvent.

* * * * *